United States Patent
Tanaka

(10) Patent No.: US 7,973,930 B2
(45) Date of Patent: Jul. 5, 2011

(54) SPECTROSCOPIC ELLIPSOMETER

(75) Inventor: Satoru Tanaka, Tokyo (JP)

(73) Assignee: HORIBA, Ltd., Kyoto (JP)

( * ) Notice: Subject to any disclaimer, the term of this patent is extended or adjusted under 35 U.S.C. 154(b) by 351 days.

(21) Appl. No.: 12/389,707

(22) Filed: Feb. 20, 2009

(65) Prior Publication Data

US 2009/0225317 A1   Sep. 10, 2009

(30) Foreign Application Priority Data

Mar. 5, 2008   (JP) ................................. 2008-055584

(51) Int. Cl.
*G01J 4/00* (2006.01)
(52) U.S. Cl. ........................................ 356/369; 356/364
(58) Field of Classification Search ............ 356/364–369
See application file for complete search history.

(56) References Cited

U.S. PATENT DOCUMENTS

| 5,835,220 A | * | 11/1998 | Kazama et al. ............... 356/369 |
| 7,196,793 B2 | * | 3/2007 | Nabatova-Gabain et al. | 356/369 |
| 7,280,210 B2 | * | 10/2007 | Nabatova-Gabain et al. | 356/369 |

FOREIGN PATENT DOCUMENTS

JP   2005/308607   11/2005

* cited by examiner

*Primary Examiner* — L. G Lauchman
(74) *Attorney, Agent, or Firm* — Alleman Hall McCoy Russell & Tuttle LLP

(57) ABSTRACT

A spectroscopic ellipsometer can compare data different in a measurement condition and facilitate setting an initial value of fitting data even for an inexperienced operator such as a beginner. The spectroscopic ellipsometer includes a reference data storage part storing therein reference data to be compared with measurement data, a conversion operation part converting the measurement data or the reference data into comparable data, so that the measurement data can be compared with the reference data, and a comparison and determination part comparing the measurement data with the reference data made comparable by the conversion operation part with each other and determining a coincidence between the measurement data and the reference data.

8 Claims, 5 Drawing Sheets

SPECTROSCOPIC ELLIPSOMETER

BACKGROUND OF THE INVENTION

1. Field of the Invention

The present invention relates to a spectroscopic ellipsometer for measuring a thickness or the like of a thin film on a surface of, for example, a glass substrate of a semiconductor wafer, a reticule/mask or a liquid crystal display (LCD).

2. Description of the Background Art

As disclosed in Japanese Unexamined Patent Publication No. 2005-308607, an ellipsometer is a device for observing a change in a polarization state when a light is reflected or transmitted by a surface of a sample and measuring optical constants (a refractive index and an extinction coefficient) of the sample or, if a thin film layer is present on the surface of the sample, measuring a layer thickness and optical constants of the thin film layer. Each specific measurement value is represented as follows using psi ($\Psi$) and delta ($\Delta$) related to a ratio of a Fresnel reflection coefficient $R_p$ of a p-polarization state and a Fresnel reflection coefficient $R_s$ of an s-polarization state:

$$\rho = R_p/R_s = \tan(\Psi)\exp(i\Delta).$$

In the Equation, $\tan(\Psi)$ is equal to an amplitude of a ratio of a p-direction complex reflection coefficient to an s-direction complex reflection coefficient and $\Delta$ denotes a phase difference between the reflection coefficients of the p-polarization state and the s-polarization state.

Meanwhile, a single-wavelength ellipsometer obtains a film thickness value from ellipsometric parameters such as tan ($\Psi$) and $\Delta$ by simple calculation. However, if a film thickness of a multilayer film is to be measured, the single-wavelength ellipsometer is required to use an extremely complicated model equation and cannot simply calculate the film thickness. Recently, therefore, development of an ellipsometer based on a method called "spectroscopic ellipsometry" for analyzing a multilayer film by performing parameter fitting and multivariate analysis while changing wavelengths is underway.

According to the spectroscopic ellipsometry method, fitting data defined by a plurality of parameters such as a film thickness, optical constants and a surface roughness of a sample is made to approximate measurement data represented by a $\Delta$ value and a $\Psi$ value at every wavelength of a reflected light with respect to an incident light irradiated on the sample by sequentially changing the respective parameters. Further, properties of the sample are calculated based on values of the respective parameters for approximated fitting data at a time at which an error of the fitting data from the measured data is estimated to be a minimum.

Currently, an ordinary fitting calculation based on the spectroscopic ellipsometry method ends at the time at which the error between the measured data and the fitting data is estimated to be a minimum, as stated above.

Fitting will now be described. If it is assumed that N measurement data pairs are Exp (i=1, 2, ..., N), N model calculation data pairs of the fitting data corresponding to the N measurement data pairs are Mod (i=1, 2, ..., N), and that a standard deviation is $\sigma_i$ on a premise that a measurement error is normally-distributed, a mean square error ($x^2$) is represented by the following Equation:

$$\chi^2 = \{1/(2N-P)\}\sum_{i=1}^{N}(Exp_i - Mod_i)^2/\sigma_i^2. \quad [\text{Equation 1}]$$

In Equation (1), P denotes a number of parameters. The fact that $x^2$ is small is none other than a high coincidence between a measurement result and a model. Accordingly, if a comparison is made for a plurality of models, a model exhibiting a smallest $x^2$ is considered a best model.

However, a fitting method using such a mean square error ($x^2$) has a problem in that the method cannot be applied to an instance in which measurement data differs from fitting data in the number of pieces of data.

Moreover, the conventional spectroscopic ellipsometer has the following problems. Generally, because of differences in a measurement condition, such as an angle of incidence (AOI) of an incident light irradiated on a surface of a sample, a wavelength measurement range and the number of pieces of data, a simple comparison cannot be made between measurement data and reference data.

Furthermore, a subsequent calculation volume increases depending on a setting of an initial value of fitting data to be parameter-fit to the measurement data, resulting in consumption of time. The setting of the initial value of the fitting data greatly depends on expertise of an operator, the setting is quite a difficult operation for a beginner and the beginner is forced to perform calculation by trial and error.

SUMMARY OF THE INVENTION

It is, therefore, an object of the present invention to provide a spectroscopic ellipsometer that can solve the conventional problems, that can compare data different in a measurement condition, and that can facilitate setting an initial value of fitting data even for an inexperienced operator such as a beginner or, to be specific, that makes it possible for the inexperienced operator to set an initial value of a dispersion formula or of a film thickness and an analysis model quite easily.

Namely, a spectroscopic ellipsometer according to an aspect of the present invention is a spectroscopic ellipsometer for approximating fitting data defined by a plurality of measurement data parameters, including a $\Delta$ value and a $\Psi$ value at every wavelength or values directly calculated from the $\Delta$ value and the $\Psi$ value by sequentially changing the parameters, and for calculating properties of a sample from values of the parameters defining the approximated fitting data. A wavelength is defined herein as a wavelength of incident light on a measurement sample or a wavelength of reflected light from the incident light.

The spectroscopic ellipsometer according to an aspect of the present invention includes a reference data storage part storing therein reference data to be compared with the measurement data, a conversion operation part for converting the measurement data or the reference data into comparable data so that the measurement data can be compared with the reference data, and a comparison and determination part for comparing the measurement data with the reference data that are made comparable by the conversion operation part, and determining a coincidence between the measurement data and the reference data.

If the spectroscopic ellipsometer is constituted as stated above, at least one of the measurement data or reference data is converted so that the measurement data can be compared with the reference data. Therefore, the spectroscopic ellipsometer according to one aspect of the present invention can compare the measurement data with the reference data irrespective of a measurement condition for the measurement data, a condition for each reference data or the like. Furthermore, the spectroscopic ellipsometer according to one aspect of the present invention automatically compares the measurement data with the reference data made comparable by converting at least one of the measurement data and each reference data and decides the coincidence between the measurement data and the reference data. Due to this, even an operator such as an inexperienced beginner can easily set an initial value of the fitting data, that is, an initial value of a dispersion formula or an initial value of a film thickness. At the same time, even the operator such as an inexperienced beginner can set an analysis model easily. It is, therefore, possible to provide a more user-friendly spectroscopic ellipsometer.

It is preferable that the reference data includes at least one of base reference data inputted in advance, analysis result data that is a result of analyzing past measurement data, and dispersion formula data indicating a dispersion formula.

A specific mode for conversion performed by the conversion operation part is, the conversion operation part preferably converts the measurement data or the reference data into comparable data based on a condition including at least one of an angle of incidence of an incident light irradiated on the sample, a wavelength measurement range, and the number of pieces of data.

The measurement data and the reference data differ in base depending on a film thickness of each layer formed on the sample and optical constants, such as a dielectric constant. Therefore, to make bases of the measurement data and the reference data coincident, it is preferable that the conversion operation part makes a baseline correction of the reference data according to the measurement data, and that the comparison determination part compares a graph pattern represented by the baseline-corrected reference data with a graph pattern represented by the measurement data.

A program used for a spectroscopic ellipsometer according to another aspect of the present invention is a program used for the spectroscopic ellipsometer, wherein the program causes a computer to execute functions as a reference data storage part storing therein reference data to be compared with the measurement data, a conversion operation part converting the measurement data or the reference data into comparable data so that the measurement data can be compared with the reference data, and a comparison and determination part comparing the measurement data with the reference data that are made comparable with each other by the conversion operation part, and determining a coincidence between the measurement data and the reference data.

As can be understood, according to the present invention, it is possible to compare data different in a measurement condition and facilitate setting an initial value of fitting data even for an inexperienced operator such as a beginner or, to be specific, it is possible for even the inexperienced operator to set an initial value of a dispersion formula or of a film thickness and an analysis model quite easily.

BRIEF DESCRIPTION OF THE DRAWINGS

FIG. 5 is a schematic diagram showing a search setting screen according to a modification of the present invention.

DESCRIPTION OF THE PREFERRED EMBODIMENTS

A spectroscopic ellipsometer according to an embodiment of the present invention will be described hereinafter referring to the accompanying drawings.

A spectroscopic ellipsometer 100 according to the present embodiment is a device for observing a change in a polarization state when a light is reflected by a surface of a sample and for measuring a film thickness, optical constants (including a refractive index and an extinction coefficient) and the like that are properties of the sample.

Figure 1:
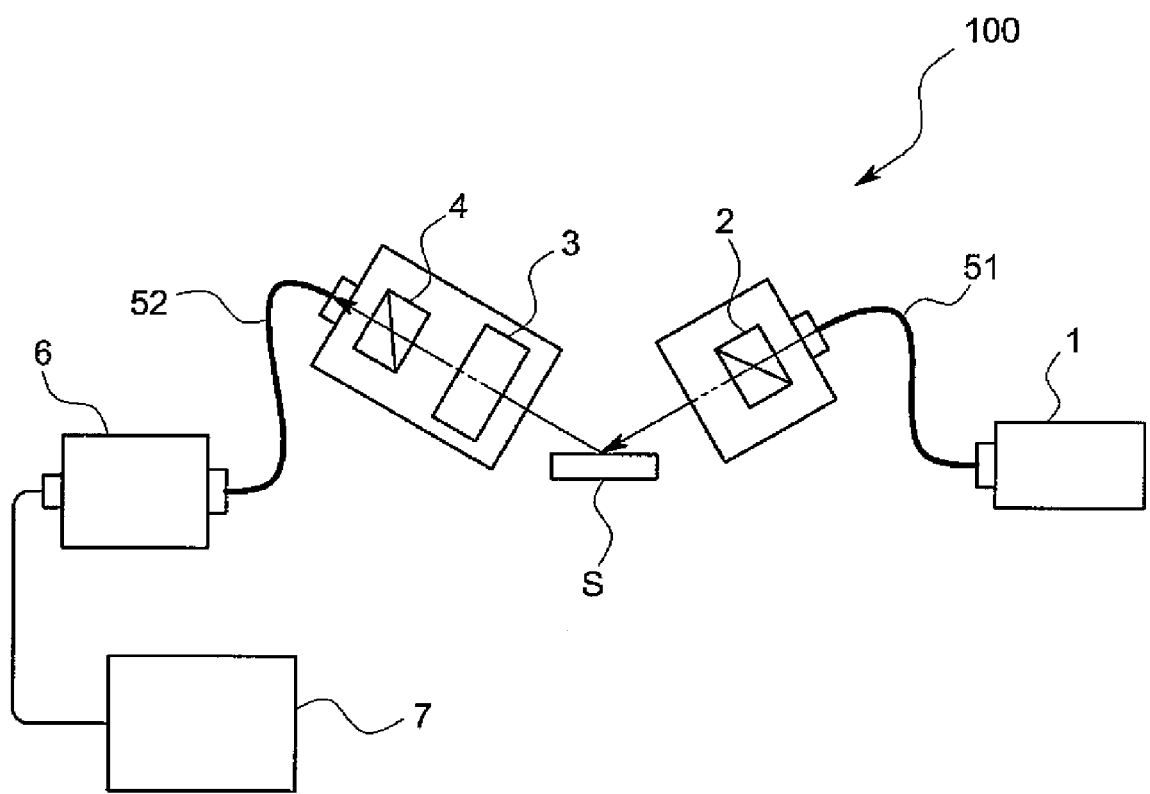
FIG. 1 is an overall pattern diagram of a spectroscopic ellipsometer according to an embodiment of the present invention.

FIG. 1 is an overall schematic diagram of the spectroscopic ellipsometer 100 according to the present embodiment. The spectroscopic ellipsometer 100 can detect $\Psi$ and $\Delta$ at high speed by an operation performed by, for example, a rotating compensator. In FIG. 1, reference symbol 1 denotes a light source that is, for example, a xenon lamp in the present embodiment. Reference symbol 2 denotes a polarizer, reference symbol 3 denotes a rotating compensator, reference symbol S denotes a sample under analysis, reference symbol 4 denotes a rotating analyzer, reference symbol 6 denotes a spectrometer and reference symbol 7 denotes an information processing device loading and processing data outputted from the spectrometer 6. Further, reference symbol 51 denotes an optical fiber for introducing a light from the light source 1 to the polarizer 2 and reference symbol 52 denotes an optical fiber for introducing light passing through the rotating analyzer 4 to the spectrometer 6.

Figure 2:
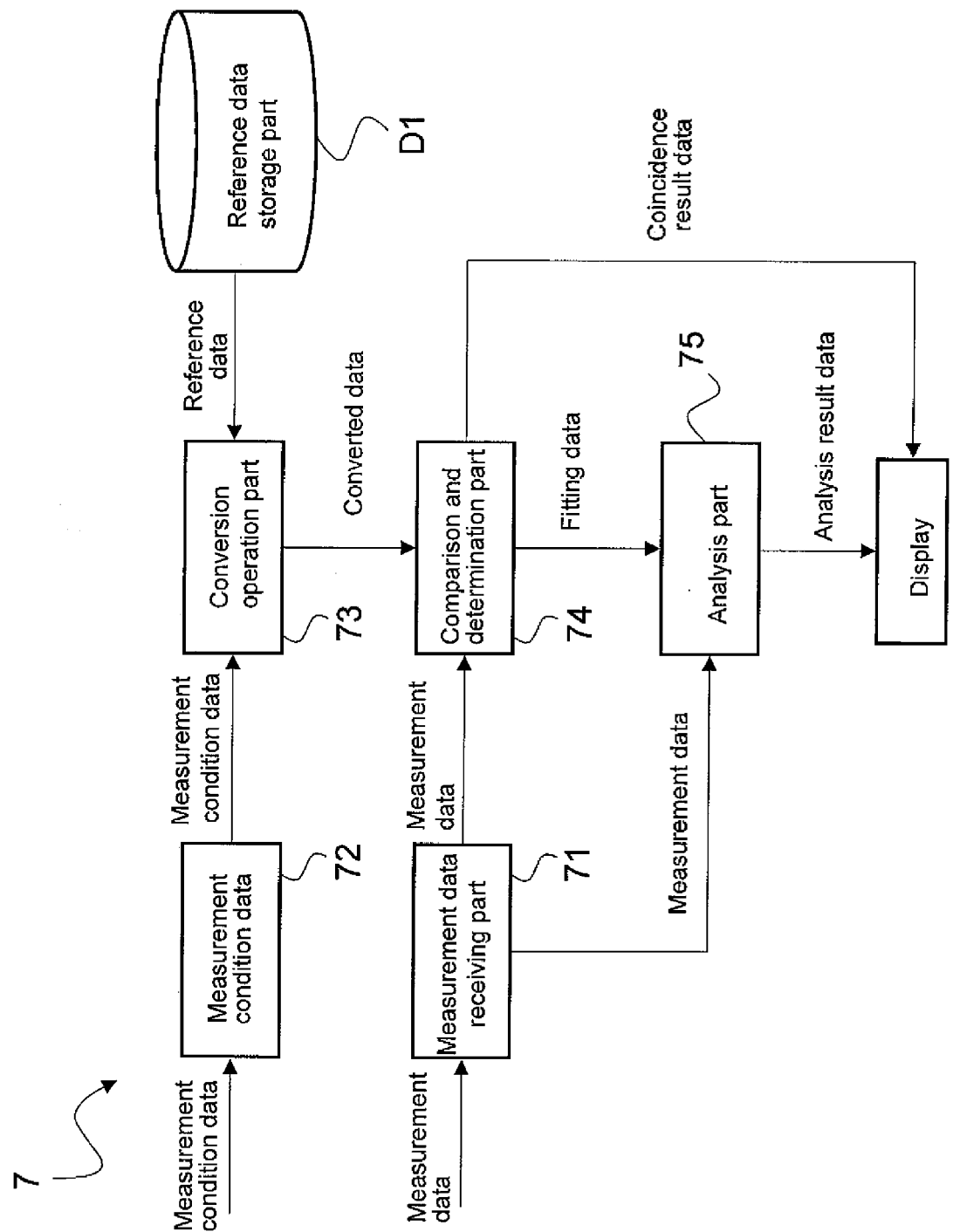
FIG. 2 is a functional block diagram of an information processing device according to the embodiment.

The information processing device 7 according to the present embodiment approximates fitting data defined by a plurality of parameters to measurement data including a $\Delta$ value and a $\Psi$ value at every wavelength or values directly calculated from the $\Delta$ value and the $\Psi$ value, and calculates properties of the sample from values of the parameters that define the fitting data. The information processing device 7 is configured to include a general-purpose or dedicated computer including a CPU, an internal memory, an input/output interface, an AD converter and the like, and input means such as a display, a keyboard and a mouse connected to the computer. In the present embodiment, the CPU, peripherals of the CPU and the like are actuated based on a program stored in a predetermined area of the internal memory. The CPU, peripherals of the CPU and the like thereby function as a measurement data receiving part 71, a reference data storage part D1, a measurement condition receiving part 72, a conversion operation part 73, a comparison and determination part 74, an analysis part 75 and the like as shown in FIG. 2.

The constituent elements 71 to 75 and D1 of the information processing device 7 will be described in detail.

Figure 3:
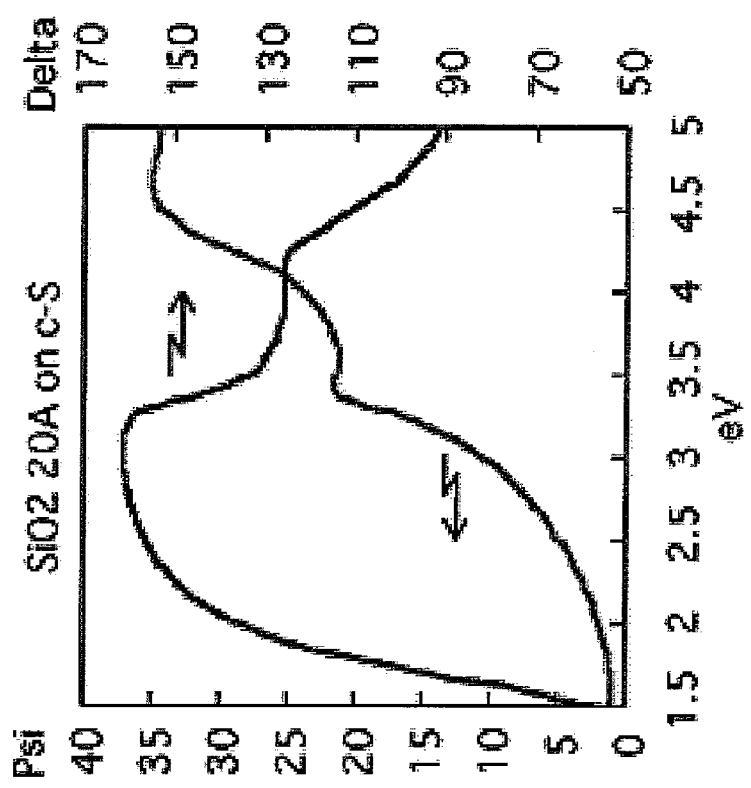
FIG. 3 is a graph showing a $\Delta$ value and a $\Psi$ value with a horizontal axis indicating energy (wavelength).

The measurement data receiving part 71 receives measurement data from the spectrometer 6. The measurement data comprises a $\Delta$ value and a $\Psi$ value at every wavelength of a reflected light with respect to an incident light on a sample. As an example, FIG. 3 shows the measurement data in the form of a graph with a horizontal axis indicating wavelength (or energy). It is to be noted that the measurement data is not limited to the $\Delta$ value and the $\Psi$ value but may be values that can be obtained directly from the $\Delta$ value and the $\Psi$ value, for example, a pseudo refractive index n', a pseudo extinction coefficient k', an $I_s$ value and an $I_c$ value (directly measured for phase modulation using a photoelastic modulator (PEM)), or may be Fresnel reflection coefficients $R_p$ and $R_s$ or the like. The measurement data receiving part 71 outputs the measurement data to the comparison and determination part 74 and the analysis part 75.

The reference data storage part D1 stores therein pieces of reference data to be compared with the measurement data. The reference data comprises each of or one or more of base reference data (document-based value), dispersion formula data (a dispersion formula, a dielectric formula), analysis result data (an analysis model) that is a result of analyzing past measurement data, spectral data (past measurement data and analysis result data associated with the past measurement data), and calculation data (data obtained by processing the base reference data, the measurement data, the spectral data or the like, such as a Ψ value and Δ value of data obtained by combining a plurality of pieces of measurement data (data of a combination of a Ψ value and a Δ value in a predetermined energy range (for example, 1.5 eV to 2 eV) of one measurement data and a Ψ value and a Δ value in a predetermined energy range (for example, 2 eV to 5 eV) of another measurement data, data obtained by combining the pieces of reference data, data obtained by combining the measurement data and the reference data, data obtained by removing noise, data obtained by partially extracting a predetermined energy range of the spectral data, the reference data or the like (data obtained by extracting a range of 2 eV to 4 eV from data in an energy range from 1.5 eV to 5 eV), data created by a user or the like). The reference data can be associated with the analysis model. The reference data storage part D1 may store at least one of these data. In this case, respective reference data are stored while being systemized according to items of a measurement condition such as the AOI. An operator may store the respective reference data in the reference data storage part using the input means or analysis results obtained during past analyses. If the measurement data is compared with the spectral data, analysis speed may be accelerated since the analysis model can be used when the measurement data and the spectral data are identical or similar in spectrum.

The measurement condition receiving part 72 receives measurement condition data indicating a measurement condition under which the measurement data is obtained from the spectrometer 6 by, for example, operator's input operation. The measurement condition is a condition that includes at least one of an AOI of an incident light, a wavelength measurement range, the number of data (a measurement pitch) and the like and that is a condition under which the measurement data is acquired. The measurement condition receiving part 72 outputs the measurement condition data to the conversion operation part 73.

The conversion operation part 73 converts each reference data according to the measurement condition when acquiring the measurement data. Specifically, the conversion operation part 73 acquires the measurement condition data inputted by an operator, acquires reference data stored in the storage part from the reference data storage part D1 and converts all reference data so as to coincide with a measurement condition under which the measurement data is acquired.

For example, if certain reference data is data at an AOI of 60 degrees and the measurement condition is an AOI of 75 degrees, the conversion operation part 73 converts the reference data into data at the AOI of 75 degrees.

Furthermore, even if the measurement data differs from the reference data in the number of pieces of data, an approximate curve is created by interpolating the reference data using an interpolation function such as a spline function so as to be able to compare the both data. The number of pieces of data on the approximate curve is made to conform to that of the measurement condition. It is thereby possible to use a fitting technique based on a mean square error ($x^2$).

The comparison and determination part 74 receives a plurality of pieces of converted data from the conversion operation part 73 and compares each of the plurality of pieces of converted data with the measurement data. At this time, a coincidence between each converted data and the measurement data is calculated by means of a method of least squares. The coincidence is indicated by a numerical value from 0% to 100%. Alternatively, the coincidence may be determined based on the numbers of peaks or peak wavelength positions of the measurement data and each reference data without using the method of least squares.

Figure 4:
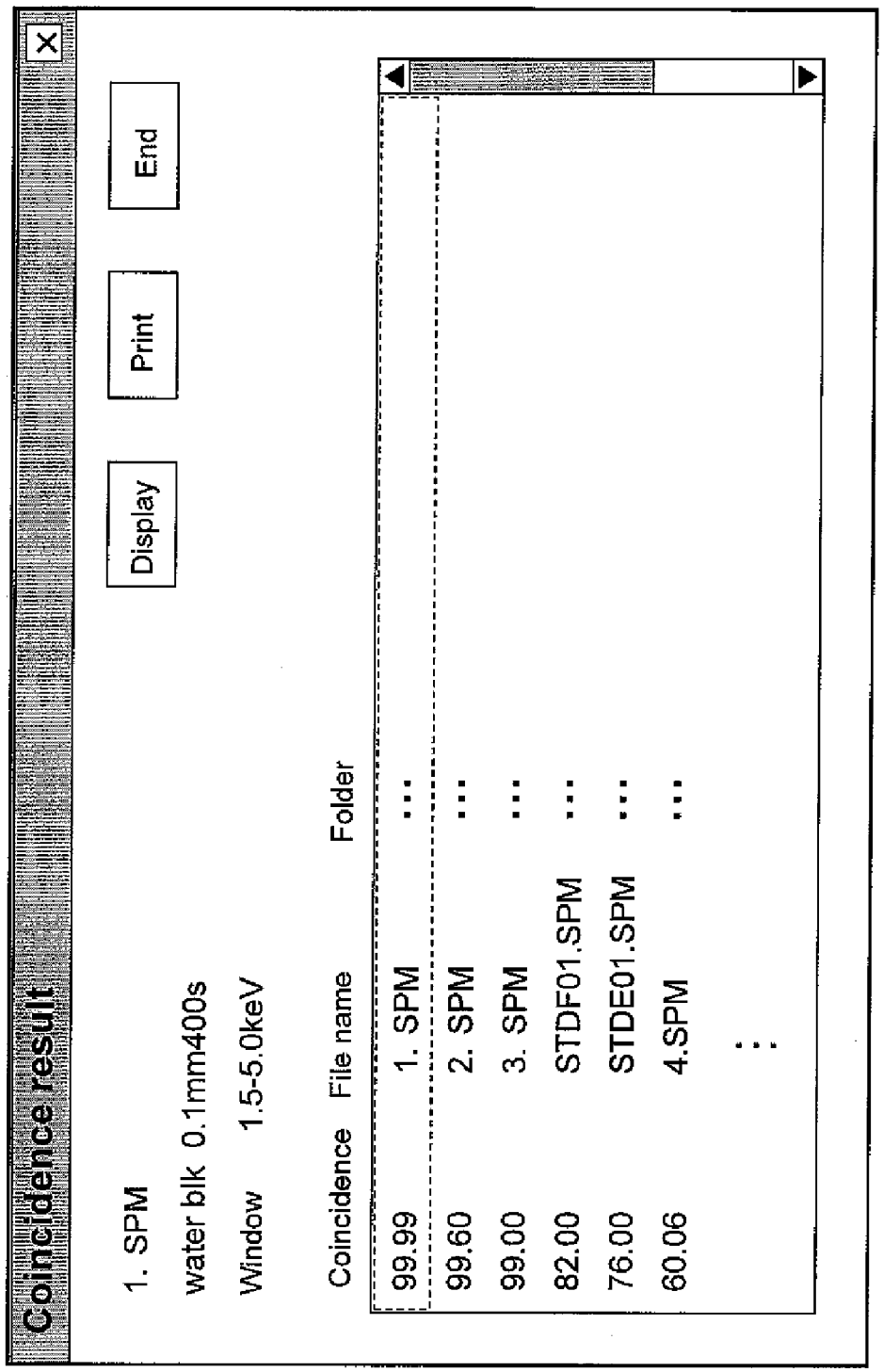
FIG. 4 is a schematic diagram showing a determination result screen on which a determination result obtained by a comparison and determination part is displayed.

Furthermore, as shown in FIG. 4, the comparison and determination part 74 rearranges the plural converted data in descending order of coincidence and displays identifiers (such as file names of pieces of original reference data before they are converted into the converted data) as well as the coincidences on a display as a coincidence result. The comparison and determination part 74 outputs reference data selected by the operator to the analysis part 75 as fitting data. At this time, the comparison and determination part 74 may decide the fitting data using the coincidences as parameters. Namely, the comparison and determination part 74 may decide reference data having a highest coincidence as the fitting data or reference data having a coincidence of 95% as the fitting data. Alternatively, the comparison and determination part 74 may decide higher or top several reference data as the fitting data. If the coincidence is about 100% (indicating that the reference data almost coincides with the measurement data), the comparison and determination part 74 sets a value of the reference data as a measurement value.

The analysis part 75 receives the measurement data from the measurement data receiving part 71 and the fitting data from the comparison and determination part 74. The analysis part 75 conducts fitting by calculating fitting data when sequentially changing a plurality of parameters defining the fitting data in the case where distributed data is used as the fitting data. As a calculation equation for this, a predetermined DSP (dispersion formula) is used. If the base reference data is used as the fitting data, the analysis part 75 conducts fitting while changing only a film thickness value. In the case where the analysis result data is used as the fitting data, the analysis part 75 conducts fitting while changing one of or each of a coefficient of the dispersion formula and the film thickness value.

Operation According to the Embodiment

An operation performed by the spectroscopic ellipsometer 100 according to the present embodiment will now be described.

When the spectrometer 6 transmits the measurement data to the information processing device 7, the measurement data receiving part 71 receives this measurement data. The measurement data receiving part 71 transmits the measurement data to the comparison and determination part 74 and the analysis part 75.

The measurement condition receiving part 72 also receives the measurement condition data from the input means and outputs the measurement condition data to the conversion operation part 73. In response to the measurement condition data, the conversion operation part 73 converts all reference data stored in the reference data storage part D1 according to the measurement condition. Thereafter, the conversion operation part 73 transmits the converted data to the comparison and determination part 74.

The comparison and determination part 74 calculates the coincidence between the measurement data and each of the converted data, rearranges the converted data in the descending order of coincidence and displays the identifiers of the converted data on the display.

The comparison and determination part 74 transmits converted data selected by the operator among the identifiers displayed on the display to the analysis part 75 as the fitting data. The analysis part 75 that has received the measurement data and the fitting data conducts fitting while sequentially changing the parameters that define the fitting data.

Advantages of the Embodiment

As stated so far, the spectroscopic ellipsometer 100 according to the present embodiment configured as stated above converts each reference data according to the measurement condition for the measurement data. Therefore, the spectroscopic ellipsometer 100 according to the present embodiment can compare the measurement data with each reference data irrespective of the measurement condition. Furthermore, the spectroscopic ellipsometer 100 according to the present embodiment automatically compares the measurement data with each reference data converted according to the measurement condition and decides the fitting data. Due to this, even an operator such as an inexperienced beginner can easily set an initial value of the fitting data, that is, an initial value of a dispersion formula or an initial value of a film thickness. At the same time, even the operator such as an inexperienced beginner can set an analysis model easily. It is, therefore, possible to provide the more user-friendly spectroscopic ellipsometer 100.

Other Modifications

The present invention is not limited to the embodiment stated above.

Figure 5:
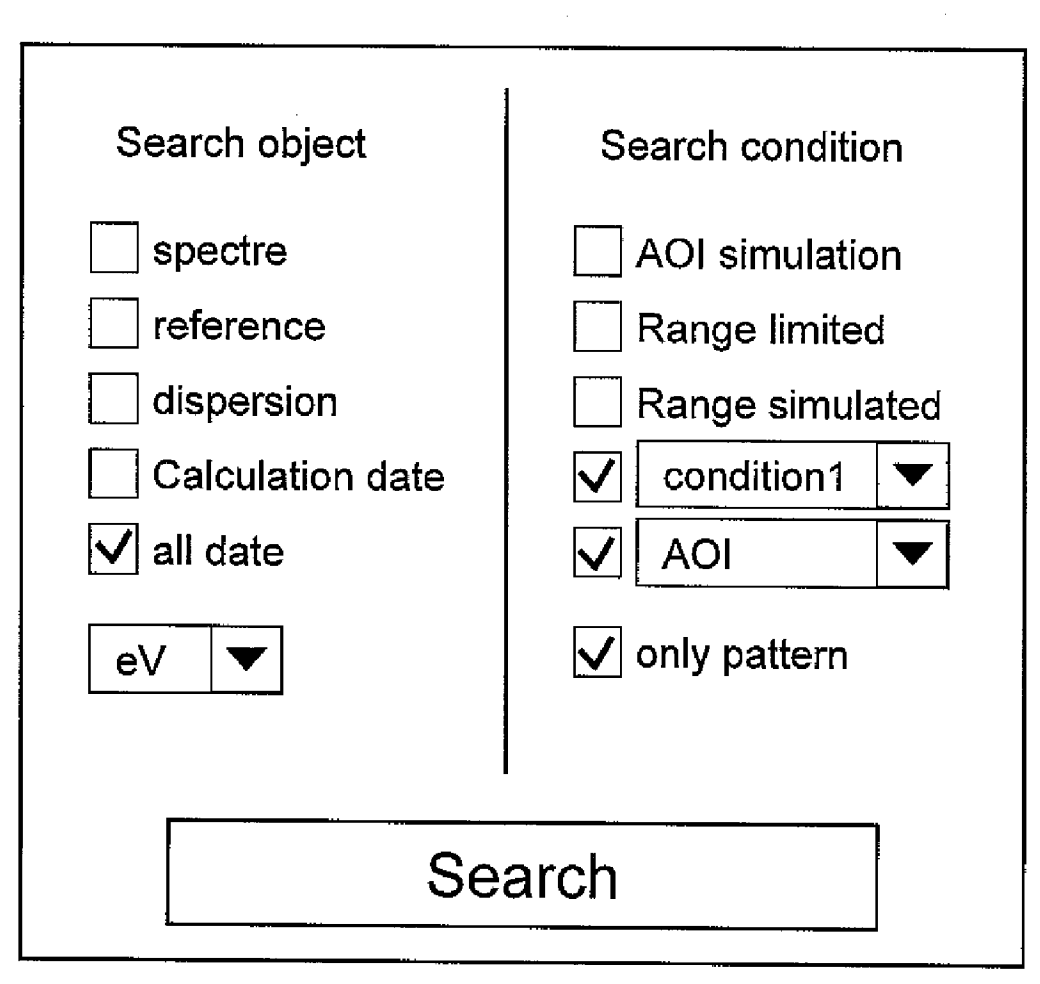

For example, in the present embodiment, the conversion operation part converts all pieces of reference data stored in the reference data storage part. Alternatively, the conversion operation part may convert a part of the reference data stored in the reference data storage part. In this alternative, as indicated by, for example, a search screen as shown in FIG. 5, the operator may select reference data to be converted. In FIG. 5, "spectral data (spectre)", "document-based data (reference)", "dispersion formula (dispersion)", "calculation data (calculation data)" and "all pieces of data (all data)" are selectable as search objects. At this time, a unit of the incident light (irradiation light) is made selectable from among energy (eV), wavelength (nm) and the like. Moreover, as a search condition, "angle of incidence simulated (AOI simulated)", "range limited (Range limited)", "range simulated (Range simulated)", "condition selection (selection of a Ψ value and a Δ value, selection of a pseudo refractive index n and a pseudo extinction coefficient k or selection of an $I_s$ value and an $I_c$ value), "selection of AOI (selection of 60 degrees, 70 degrees or 75 degrees or input of an arbitrary angle) and "only pattern (only pattern)" are made selectable. The reason for making "only pattern (only pattern)" selectable is that data differs in an amplitude value or a base according to a difference in a thickness or a dielectric constant.

If a search is conducted while selecting "only pattern (only pattern)" as the search condition, it is preferable that the conversion operation part makes a baseline correction of searched reference data according to the measurement data, and that the comparison and determination part compares a graph pattern represented by the corrected reference data with that represented by the measurement data.

Alternatively, pieces of reference data may be divided into groups and stored in the reference data storage part according to the groups. In this case, pieces of data may be divided into groups according to frequencies of use at each of which a predetermined sample is measured or pieces of reference data may be divided into groups according to similarities in condition. Furthermore, only the reference data belonging to one or a plurality of groups selected from among a plurality of groups based on the measurement condition and the like may be converted.

Moreover, the dispersion formula data stored in the reference data storage part may be stored to correspond to names of substances so as to be able to search the dispersion formula data based on the name of a substance.

Additionally, searched information may be linked to the reference data set as the fitting data (initial value) so that the searched information can be invoked from the reference data.

The spectroscopic ellipsometer may also include a search part that searches each reference data stored in the reference data storage part using the analysis result data (such as the dispersion formula data) obtained from the analysis part and a determination part that compares a refractive index, a waveform pattern, parameters and the like indicated by the reference data obtained from a known substance searched by the search part with the refractive index, the waveform pattern, the parameters and the like indicated by the analysis result data and that determines whether or not the analysis result is valid. If the spectroscopic ellipsometer includes these parts, it is possible to automatically determine whether or not the analysis result is correct (automatically make a validity check) and prevent an error resulting from an operator's determination. Alternatively, the reference data searched by the search part and the analysis result data may be displayed on the display without providing the determination part in the spectroscopic ellipsometer.

The measurement condition receiving part may receive the measurement condition data from the spectroscope or the like.

In the above-described embodiment, the conversion operation part converts each reference data according to the measurement condition under which the measurement data is acquired. Alternatively, the conversion operation part may convert the measurement data according to a condition under which each reference data is acquired. In this case, the comparison and determination part compares each reference data with the converted measurement data and calculates a coincidence between the reference data and the converted measurement data. In another alternative, the conversion operation part may convert both the measurement data and each reference data according to one common condition. In this case, the comparison and determination part compares each converted reference data with the converted measurement data and calculates a coincidence between the converted reference data and the converted measurement data. Namely, it suffices that the conversion operation part converts at least one of the measurement data and each reference data so as to be able to compare the measurement data with each reference data under the same condition. In other words, it suffices that the conversion operation part converts at least one of the measurement data and each reference data so that the measurement data and each reference data are identical in condition.

Moreover, in the above-described embodiment, the analysis model is associated with the analysis result data and the spectral data. Alternatively, the analysis model may be associated with various types of reference data such as other base reference data or calculation data.

Furthermore, the spectroscopic ellipsometer may decide a sample model in advance using the analysis model associated with each reference data and then conduct fitting to measure data. If the spectroscopic ellipsometer is thus configured, even an operator such as an inexperienced beginner can easily set the analysis model.

The data obtained by combining the reference data and the model of the sample can be used as new reference data.

Needless to say, the above-stated embodiment and the modifications may be appropriately combined either partially or entirely, and the present invention is not limited to the embodiment and the modifications, but can be variously changed or modified within a scope without departure from the spirit of the present invention.

What is claimed is:

1. A spectroscopic ellipsometer for approximating fitting data defined by one or a plurality of parameters to measurement data including a $\Delta$ value and a $\Psi$ value at every wavelength or values directly calculated from the $\Delta$ value and the $\Psi$ value by sequentially changing the parameters, and for calculating properties of a sample from values of the parameters defining the approximated fitting data, the spectroscopic ellipsometer comprising:
   a reference data storage part storing therein reference data to be compared with the measurement data;
   a conversion operation part converting the measurement data or the reference data into comparable data so that the measurement data is comparable with the reference data; and
   a comparison and determination part comparing the measurement data with the reference data that are made comparable by the conversion operation part with each other, and determining a coincidence between the measurement data and the reference data.

2. The spectroscopic ellipsometer according to claim 1, wherein the reference data includes at least one of base reference data inputted in advance, analysis result data that is a result of analyzing past measurement data, and dispersion formula data indicating a dispersion formula.

3. The spectroscopic ellipsometer according to claim 1, wherein the conversion operation part converts the measurement data or the reference data into the comparable data based on a condition including at least one of an angle of incidence of an incident light irradiated on the sample, a wavelength measurement range, and the number of pieces of data.

4. The spectroscopic ellipsometer according to claim 2, wherein the conversion operation part converts the measurement data or the reference data into the comparable data based on a condition including at least one of an angle of incidence of an incident light irradiated on the sample, a wavelength measurement range, and the number of pieces of data.

5. The spectroscopic ellipsometer according to claim 2, wherein the conversion operation part makes a baseline correction of the reference data according to the measurement data, and
the comparison determination part compares a graph pattern represented by the baseline-corrected reference data with a graph pattern represented by the measurement data.

6. The spectroscopic ellipsometer according to claim 3, wherein the conversion operation part makes a baseline correction of the reference data according to the measurement data, and
the comparison determination part compares a graph pattern represented by the baseline-corrected reference data with a graph pattern represented by the measurement data.

7. The spectroscopic ellipsometer according to claim 4, wherein the conversion operation part makes a baseline correction of the reference data according to the measurement data, and
the comparison determination part compares a graph pattern represented by the baseline-corrected reference data with a graph pattern represented by the measurement data.

8. A program for a spectroscopic ellipsometer for approximating fitting data defined by a plurality of parameters to measurement data including a $\Delta$ value and a $\Psi$ value at every wavelength or values directly calculated from the $\Delta$ value and the $\Psi$ value by sequentially changing the parameters, and for calculating properties of a sample from values of the parameters defining the approximated fitting data, the program causing a computer to execute functions as:
   a reference data storage part storing therein reference data to be compared with the measurement data;
   a conversion operation part converting the measurement data or the reference data into comparable data so that the measurement data can be compared with the reference data; and
   a comparison and determination part comparing the measurement data with the reference data that are made comparable by the conversion operation part with each other, and determining a coincidence between the measurement data and the reference data.

* * * * *